United States Patent [19]
Helldin

[11] Patent Number: 5,624,408
[45] Date of Patent: Apr. 29, 1997

[54] SYRINGE

[75] Inventor: Nils G. Helldin, Götene, Sweden

[73] Assignee: Dille Safe AB, Ås, Sweden

[21] Appl. No.: 387,945

[22] PCT Filed: Aug. 23, 1993

[86] PCT No.: PCT/SE93/00698

§ 371 Date: May 9, 1995

§ 102(e) Date: May 9, 1995

[87] PCT Pub. No.: WO94/04208

PCT Pub. Date: Mar. 3, 1994

[30] Foreign Application Priority Data

Aug. 25, 1992 [SE] Sweden ................... 9202423

[51] Int. Cl.$^6$ ........................................... A61M 5/315
[52] U.S. Cl. ........................ 604/224; 604/228; 604/110
[58] Field of Search ............................. 604/224, 110,
604/218, 233, 240, 228, 229, 195, 196,
242, 243

[56] References Cited

U.S. PATENT DOCUMENTS

| 4,391,272 | 7/1983 | Staempfli. | |
|---|---|---|---|
| 4,775,364 | 10/1988 | Alles. | |
| 5,007,904 | 4/1991 | Densmore et al. | 604/228 |
| 5,059,179 | 10/1991 | Quatrochi et al. | 604/110 |
| 5,084,017 | 1/1992 | Maffetone | 604/110 |
| 5,181,912 | 1/1993 | Hammett | 604/110 |

FOREIGN PATENT DOCUMENTS

| 2197792 | 6/1988 | United Kingdom. |
| WO88/02640 | 4/1988 | WIPO. |
| WO89/04677 | 6/1989 | WIPO. |
| WO92/18180 | 10/1992 | WIPO. |

*Primary Examiner*—V. Millin
*Assistant Examiner*—V. Alexander
*Attorney, Agent, or Firm*—Burns, Doane, Swecker & Mathis

[57] ABSTRACT

The invention relates to a syringe (1) which comprises a rod (5) mounted for reciprocating movement in relation to a container (8), wherein one end of the rod has the form of a needle (3) or is able to coact with a needle. The syringe further comprises a piston (4) and coupling member (6) which connect and disconnect the piston to and from the rod. The coupling member assumes a connecting state when the piston is drawn by the rod from a position proximate to the needle to a position in which it is distanced therefrom, and are brought to a disconnecting or disconnected state when the piston is pressed by the rod towards the needle. The coupling member comprises support and/or slide surfaces (5k', 5k) arranged on that part of the rod which is proximal to the needle, and opposing support and/or slide surfaces (4k', 4k) on the piston. The first support and/or slide surfaces (4k') provided on the piston and located nearest the needle (3) are inclined (c) to an extent such that as the rod (5) moves towards the needle (3), the piston (4) is rotated about a container center line, among others.

11 Claims, 1 Drawing Sheet

SYRINGE

TECHNICAL FIELD

The present invention relates generally to a syringe and more particularly, although not exclusively, to a syringe which is intended for one time use only, i.e. a so-called disposable syringe, and which is of the kind that includes a rod which is fitted in a container for reciprocating movement in relation thereto and one end of which has the form of or coacts with a needle, a piston which is able to coact with the rod, and coupling means which function to connect and disconnect the piston to and from the rod.

The present invention is primarily intended to provide a syringe of this kind which is constructed so as to enable the container to be filled with liquid through the needle and the liquid then dispensed through said needle and so that after this the container can no longer be filled with and emptied of liquid.

The present invention pertains in particular to a syringe of the kind in which the coupling means which function to connect and disconnect the piston to and from the rod adopt an active coupling state over a movement path in which the piston is drawn by the rod from a position close to the needle to a position in which it is distanced from said needle, and is brought to a disconnected state when the piston is pressed by the rod through an adapted short movement path in a direction towards the needle, said coupling means comprising support and/or slide surfaces which are provided on that part of the rod which lies proximal to the needle and which coact with opposing support and/or slide surfaces on the piston in the coupled state of the rod and the piston.

BACKGROUND ART

Disposable syringes of the aforedescribed kind, by which is meant syringes that can only be used once, can be divided into a number of function-dependent categories with regard to their function-dependent characteristics.

A first syringe category is exemplified by the syringe illustrated and described in the International Patent Publication PCT/SE88/00634, International Publication No. WO 89/04677. In the case of this syringe, the rod can be twisted in relation to the container and the piston so as to move the coupling means on the one hand to a connecting state and on the other hand to a disconnecting state, as the rod is twisted. Thus, with this type of syringe, it is necessary that the piston is unable to twist or rotate or at least not essentially, at the same time as the rod is twisted in relation to the container.

It is thus of great importance with this category of syringe that means are provided to ensure that the piston will not twist together with the rod.

In a second syringe category, the rod, or red unit, carries a piston or piston unit and moves backwards and forwards in the container without twisting, and the outer surface of the piston unit and the inner surface of the container include means which mutually coact to lock the piston in a lowermost position. Examples of these prior art syringe assemblies are described and illustrated in prior publications U.S. Pat. Nos. 4,391,272; 4,775,364; PCT/GB87/00728 with respective International Publication Nos. WO 88/02640; GB-A 2,197,792 and FR-A 2,613,628.

A third category of disposable syringes includes a rod unit which is moved forwards and backwards in the container without twisting, and a piston unit which is fastened to the rod unit by means of a separate connecting part.

This connecting part is pivotally mounted on the rod part for rotation about a centre line on the rod, the piston and the container, and can be guided into to different rotational positions by grooves disposed on the piston unit.

An example of this type of syringe is described and illustrated in publication NO-A 163,263.

DISCLOSURE OF THE PRESENT INVENTION

TECHNICAL PROBLEMS

When studying the earlier known art as described above, while considering the comprehensive efforts that have been made to construct a disposable syringe which is well adapted for mass production at a cost which is comparable with the cost of manufacturing standard reusable syringes, it will be seen that a qualified technical problem is one of realizing the possibility of moving the coupling means for connecting and disconnecting the piston to and from the rod to a desired connecting and desired disconnecting state or position, solely by providing conditions which will enable the piston to be rotated within the container.

Another technical problem is one of realizing the significance of providing conditions such that rectilinear movement of the rod in the container towards the needle, without twisting the rod, will cause desired rotation of the piston so that the piston unit will cease to coact with the rod unit upon restricted rotational movement, such as rotation through less than one-half revolution.

Another technical problem is one of realizing the significance of adapting the supporting and/or sliding surfaces on the piston unit and/or the rod unit and by inclining said surfaces at an appropriate angle.

A further technical problem is one of realizing the significance of adapting the configuration of the opposing support and/or slide surfaces so as to adapt said surfaces to a desired degree of friction, and/or to a form in which they can be conveniently produced in a mould die.

Still another technical problem is one of realizing the advantages that are gained with regard to the operation of a syringe which is so constructed that when the piston is moved towards the needle so as to inject liquid contained in the container, the piston will generate a well-defined frictional force against the inner wet surface of the container, and therewith to realize the significance of choosing an appropriate angular value while considering the occurrent readily definable frictional conditions.

It will also be seen that a technical problem resides in realizing the significance of allowing the first support and/or slide surfaces provided on the piston proximal to the needle to slope at such an angle that as the rod is moved towards the needle, the piston will be twisted about a centre line on the container, among other centre lines, so as to bring said coupling means from a connected to a disconnected state in response to movement of the rod along a short movement path.

It will also be seen that a technical problem resides in realizing the significance of inclining said surfaces faces such that as the piston is rotated by the mutually coacting surfaces over a chosen initial movement path, which at least equals less than half the maximum movement path of the rod in the container, the first support and/or slide surfaces on the piston will be distanced from corresponding first support and/or slide surfaces on the rod to a position in which the coacting surfaced of said coupling means are disconnected.

It will also be seen that a technical problem resides in realizing the significance of displacing the piston and the rod to a mutually disconnected position over a small distance of less than one-quarter of the maximum movement path of the rod while still providing the desired function.

Another technical problem is one of realizing the significance of configuring the first support and/or slide surfaces on the rod so that said surfaces will coact selectively with corresponding first support and/or slide surfaces on the piston, wherein said contact surfaces can be either flat surfaces or linear surfaces, or alternatively punctiform surfaces, where at least the two latter surfaces shall slide against a continuous, preferably curved slide surface.

Another technical problem is one of realizing the significance of inclining the first support and/or slide surfaces on the piston and/or on the rod at a well-adapted angle to a centre line on the piston or the rod, among others.

A further technical problem is one of realizing the significance of inclining the second support and/or slide surfaces that are provided on the piston distal from the needle at an angle such that as the rod is moved away from the needle, the piston will be subjected to a force which acts on the second support and/or slide surfaces on the rod such as to rotate the piston around a container centre line, said second support and/or slide surfaces holding the corresponding second support and/or slide surfaces in a mutually coacting or mutually engaging position.

Another technical problem is one of realizing the significance of adapting the configuration of the second support and/or slide surface on the rod to the second support and/or slide surface on the piston.

When considering the aforesaid circumstances, it will also be seen that a technical problem resides in the ability to choose angular limit values which will not only ensure a desired and positive aspiration function but also a positive function with respect to the remainder of the disposable syringe.

SOLUTION

With the intention of solving one or more of the aforesaid technical problems, the present invention departs from a syringe of the kind which includes a rod that can be moved reciprocatingly in relation to a container and one end of which is in the form of a needle or is intended to coact with a needle, and which further includes a piston which coacts with the rod, and coupling means for connecting and disconnecting the rod to and from the piston.

The coupling means which function to connect and disconnect the piston to and from the rod are mutually engaged when the piston is drawn by the rod from a needle-proximate position to a needle-distanced position, and is brought to a disconnecting and disconnected state when the piston is pressed initially by the rod through an adapted short movement path in a direction towards the needle, said coupling means comprising support and/or slide surfaces on that part of the rod which is proximal to the needle and corresponding opposing support and/or slide surfaces on the piston, said surfaces coacting mutually in the coupled state of said coupling means.

In accordance with the invention, the first support and/or slide surfaces of the piston located nearest the needle are inclined to an extent such that as the rod is moved initially towards the needle, the piston is rotated about a container centre line, among others.

According to preferred embodiments that lie within the scope of the invention, the extent to which the piston is rotated by the inclined surfaces is adapted so that during said rod movement and after movement along a short movement path, which is less than half the maximum path of movement of the red in the container, the first support and/or slide surfaces on the piston will leave the corresponding first support and/or slide surfaces on the rod so as to bring said coupling means to a disengaged state.

The angle at which said surfaces are inclined is preferably so adapted that the distance through which the red moves in order to achieve aspiration can be chosen to be smaller than one-quarter of the maximum distance moved by the rod in the container.

According to one embodiment, the first support and/or slide surfaces on the rod may be configured for parallel, linear or punctiform cooperation with corresponding first support and/or slide surfaces on the piston.

It is especially preferred that the first support and/or slide surfaces on the piston and/or on the rod define an angle of between 85° and 20° with a centre line on the piston or the rod, among others.

One advantage afforded by the present invention is that the rod, in a known manner, can now be made straight and adapted for movement up and down in the container without twisting, with the inclusion of an associated simplified rod attachment and rod guide in the upper container part.

Furthermore, the second support and/or slide surfaces on that part of the piston which is distal from the needle are inclined to such an extent that as the rod is moved away from the needle, the piston will be subjected to a force which causes the piston to be rotated around a container centre line, among others, by the second support and/or slide surfaces on the rod, these latter surfaces holding the piston and its corresponding second support and/or slide surfaces in a coacting or co-engaging position.

According to one embodiment, the second support and/or slide surfaces on the rod are configured for parallel, linear or punctiform coaction with corresponding second support and/or slide surfaces on the piston.

ADVANTAGES

Those advantages primarily associated with an inventive disposable syringe are that the aforesaid coupling means remains in a coupled state when the piston is drawn by the rod from a position proximate to the needle to a position distanced therefrom, and are brought to a disconnecting or disconnected state when the piston is then pressed initially by the rod towards the needle, in that during axial movement in the container along a short displacement path, the first support and/or slide surfaces coacting on the piston and the rod will cause the piston to rotate so as to cause said coupling means to take a disengaging position, this being achieved solely by adapting the slope of the first support and/or slide surfaces in relation to a piston centre line or a container centre line, among others.

The primary characteristic features of an inventive disposable syringe are set forth in the characterizing clause of the following Claim 1.

BRIEF DESCRIPTION OF THE DRAWINGS

An exemplifying embodiment at present preferred and having properties significant to the present invention will now be described in more detail with reference to the accompanying drawings, in which.

BEST MODE OF CARRYING OUT THE INVENTION

Figure 1:
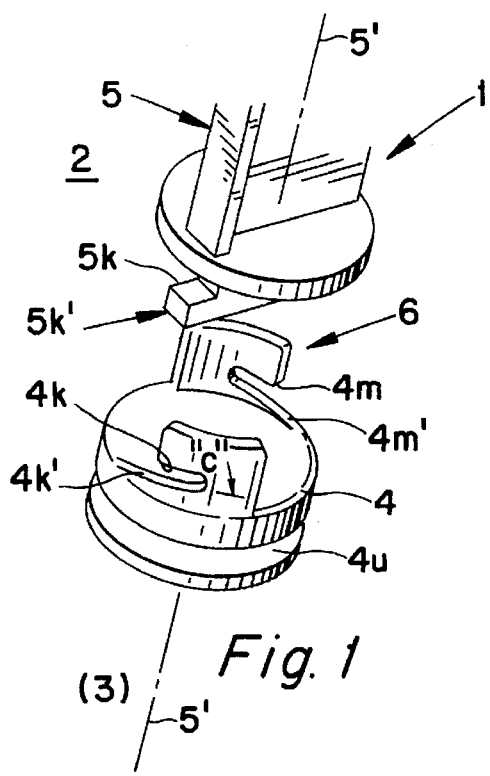
FIG. 1 is a perspective view of the lower part of a rod and associated support and/or slide surfaces, and a piston with associated support and/or slide surfaces, and shows said surfaces ill a mutually distanced and mutually disengaged position.

Because the inventive syringe can be considered to constitute a direct development of the disposable syringe illustrated and described in International Patent Publication PCT/SE92/00258, reference is made to this publication for a closer description of the different components of the syringe and the manner in which they coact with one another.

To simplify matters, the same reference signs as those used in the aforesaid international patent publication have been used in the present drawing to identify similar components.

Thus, it can be seen that the present invention is based on a syringe 1 which comprises a rod 5 that can be moved reciprocatingly in relation to a container. One end of the rod 5, the lower end, has the form of a needle 3 (not shown) or is able to coact with said needle, a piston which coacts with the rod, and coupling means 6 which function to connect and disconnect the piston to and from the rod.

As shown in FIGS. 2-7, the opposing surfaces of the coupling means 6 are mutually engaged as the piston is drawn by the rod from a position proximate to the needle 3 to a position in which the piston is distanced from the needle, and are disengaged when the piston 4 is pressed by the rod towards the needle 3. In the case of the first mentioned movement, the part 5a' is located further to the right than is shown in the Figures.

FIG. 1 illustrates an operational state of the syringe in which the piston is located in its lower-most position upon completion of injecting the contents of the syringe, with the rod withdrawn slightly upwards without coacting with the piston.

The coupling means 6 is comprised of support and/or slide surfaces provided on that part 5a' of the rod which is proximal to the needle, and coacting, opposing and corresponding support and/or slide surfaces on the piston.

Figure 2:
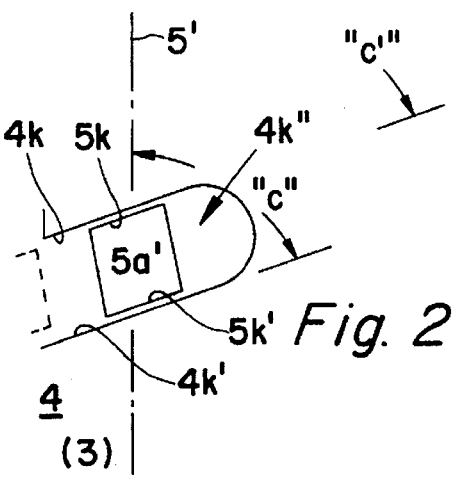
FIG. 2 is a side view showing flat support and/or slide surfaces on the rod in engagement with flat support and/or slide surfaces on the piston, with the illustrated angular values being related to a centre line on the piston and the rod, among others.

FIG. 2 illustrates clearly the significant characteristics of the present invention, wherein the first support and/or slide surfaces 4k' provided on the piston 4 and located proximal to the needle 3 slope to such an extent that as the rod 5 is moved towards the needle 3, the piston 4 is rotated about a centre line 5' of the container 8, the rod, or the piston.

Naturally, rotational movement of the piston 4 in response to axial movement of the rod 5 will depend to a very large extent on the angle at which the support and/or slide surface 4k' are inclined. According to the present invention, the slope of said surfaces is adapted so that the first support and/or slide surfaces on the piston will move away from the corresponding first support and/or slide surfaces on the rod over a chosen short movement path, which is shorter than half the maximum movement path of the rod in the container 3, so as to mutually disengage the coupling means. This is shown in broken lines in FIG. 2.

The aforesaid movement path is conveniently chosen to correspond to a distance which is shorter than one-quarter of the maximum movement path of the rod, for instance a movement path which is shorter than 10 mm, normally somewhat shorter than 5-7 mm, to provide an aspiring function.

The first support and/or slide surfaces 5k' on the rod are configured so as to be parallel with the corresponding first and/or slide surfaces 4k' on the piston, as clearly shown in FIG. 2.

There is nothing to prevent the slide surfaces 4k and/or 4k' from being curved, however, although the curve will preferably be continuous.

It is particularly recommended that the first support and/or slide surfaces on the piston and/or on the rod define an angle "c" of between 85° and 20° with a piston centre line or rod centre line 5'.

This angular value lies within those limits within which a practical function can be obtained, and a longer aspiration path is obtained at the lower values.

The surfaces may also be sloped at an angle which is adapted to the requisite sliding function.

A suitable angular value is between 80° and 45°, preferably between 75° and 65°.

FIG. 1 shows an angular value of about 80°, whereas FIGS. 2-5 show an angular value of about 70°.

The rod 5 is straight and is adapted for rectilinear, reciprocating movement in the container 3 without twisting.

The second support and/or slide surfaces 4k located on the piston distal from the needle 3 slope to an extent such that in coaction with the second support and/or slide surfaces 5k on the rod, the piston will be subjected to a force which causes the piston to rotate about a container centre line, among other centre lines, as the rod 5 is moved away from the needle, wherein the second support and/or slide surfaces 5k on the rod hold the corresponding second support and/or slide surfaces 4k in a mutually coacting or mutually engaging position.

In the case of the FIG. 2 embodiment, the second support and/or slide surfaces 5k on the rod are parallel with the corresponding second support and/or slide surfaces 4k on the piston.

The angle "c" and the length of the groove can thus be chosen in accordance with the desired maximum aspiration length of the rod, among other things, and the maximum movement path desired between fully coacting or fully engaged position of the coupling means 6 and a guaranteed disengagement position.

The angle "c" shall thus be chosen so that as the rod 5 is moved away from the needle 3, the piston will be rotated into a fully coacting position, as illustrated by the position 4k".

In the exemplifying embodiment, the angular values "c" and "c'" are identical, although there is nothing to prevent these angles being different to one another.

It should be noted in this regard that as the piston 4 is moved towards the needle 3, the peripheral surface of the piston will slide along wet internal container surfaces, and that well-defined frictional conditions prevail during this movement of the piston, these conditions being observed primarily when choosing tile value of the angle "c".

When moving the piston 4 away from the needle 3, the piston will slide along dry surfaces and the frictional conditions are more difficult to define. This circumstance should be taken into account when choosing the value of the angle "c'".

Figure 3:
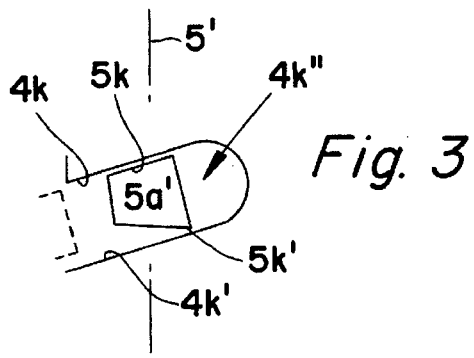
FIGS. 3-5 are side views of alternative configurations of the support and/or slide surfaces on the rod.

FIG. 3 illustrates an embodiment in which the support and/or slide surface 5k' on the rod provides a linear or punctiform abutment surface with the flat or angled first support and/or slide surface 4k' on the piston.

The second support and/or slide surface 5k on the rod is flat and can coact with a flat or linear abutment surface against the second support and/or slide surface 4k on the piston.

Figure 4:
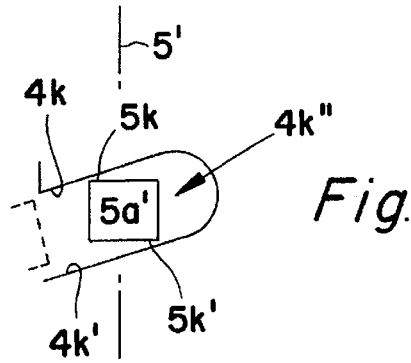

FIG. 4 illustrates an embodiment in which the support and/or slide surfaces on the rod 5 provide linear or punctiform abutment surfaces 5k' and 5k, corresponding to the configuration of the support and/or slide surfaces on the piston 4.

Figure 5:
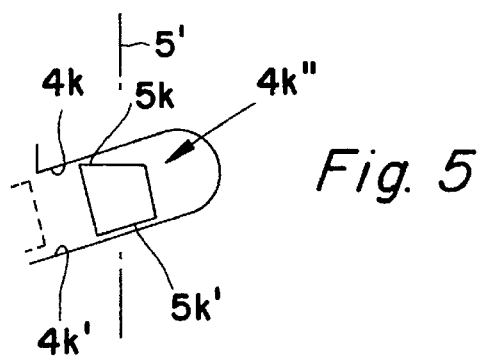

The embodiment illustrated in FIG. 5 includes a flat first support and/or slide surface 5k' and a linear second support and/or slide surface 5k.

Figure 6:
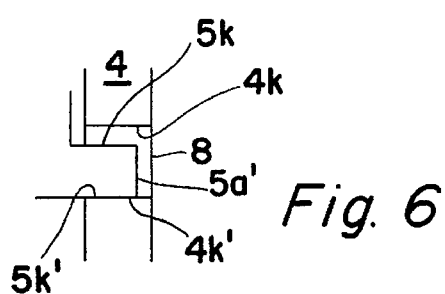
FIG. 6 illustrates a linear coaction surface between the support and/or slide surfaces of the piston and the rod.
Figure 7:
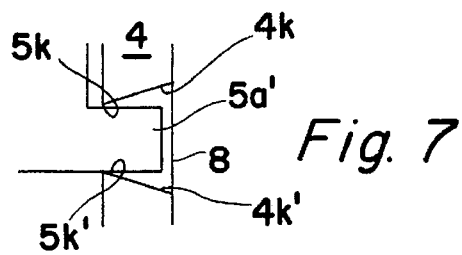
FIG. 7 illustrates a punctiform coaction surface between the support and/or slide surfaces of the piston and the rod.

In the case of the FIG. 6 embodiment, the first and second support and/or slide surfaces 4k' and 4k on the piston 4 are flat and parallel, whereas in the FIG. 7 embodiment the surfaces 4k' and 4k are flat and inwardly converging. (There is nothing to prevent the surfaces from converging outwards).

As will be understood, it is conceivable within the scope of the invention to combine each detail in FIGS. 2–5 with each detail in FIGS. 6 and 7.

Depending on the chosen angle "c", it can be assumed that in the case of small angular values, the piston is able to rotate without moving longitudinally or while moving only slightly in a longitudinal direction, whereas in the case of large angular values, the piston will rotate whilst moving in a longitudinal direction.

The invention is based on forcibly guiding movement of the rod in the container in a manner which makes it impossible to rotate or twist the rod in relation to the container and therewith effect unpermitted engagement and disengagement of the coupling means 6, irrespective of whether the rod is moving or stationary.

The guide means herefor may conveniently be mounted within the open part of the container distal from the needle 3.

It will be understood that the invention is not restricted to the aforedescribed and illustrated exemplifying embodiments thereof and that modifications can be made within the scope of the invention defined in the following Claims.

I claim:

1. A syringe comprising:

a container having a center line, a piston end, and a needle end;

a rod which can be moved reciprocatingly within the container;

a piston which coacts with the rod, and coupling means for connecting and disconnecting the piston to and from the rod, said coupling means assumes a connected state when the piston is drawn by the rod from a position proximate to the needle end toward the piston end, and the coupling means is brought to a disconnected state when the piston is pressed by the rod towards the needle end, said coupling means includes surfaces on a part of the rod which is proximal to the needle end and includes opposing and coacting surfaces on the piston, a first one of the surfaces located on the piston is inclined at an inclination to an extent such as to cause the piston to rotate about the center line as the rod moves towards the needle end.

2. A syringe according to claim 1, wherein the inclination is such that as the rod moves towards the needle end a distance less than one-half of a maximum movement path of the rod in the container, the piston will rotate so as to disengage the first surface on the piston from a corresponding first one of the surfaces on the rod and therewith bring the coupling means to the disconnected state.

3. A syringe according to claim 2, wherein said distance is less than one-quarter of the maximum movement path of said rod.

4. A syringe according to claim 3, wherein one of the surfaces on the part of the rod is configured for parallel, linear or punctiform coaction with the first surface on the piston.

5. A syringe according to claim 2, wherein one of the surfaces on the part of the rod is configured for parallel, linear or punctiform coaction with the first surface on the piston.

6. A syringe according to claim 1, wherein one of the surfaces on the part of the rod is configured for parallel, linear or punctiform coaction with the first surface on the piston.

7. A syringe according to claim 1, wherein one of the surfaces on the part of the rod defines an angle of between 85° and 20° with the center line.

8. A syringe according to claim 1, wherein the rod is straight and is mounted so as to move reciprocatingly in the container without twisting.

9. A syringe according to claim 1, wherein a second of the surfaces on the piston is located distal from the needle end and is so inclined that as the rod is moved away from the needle end a second of the surfaces on the rod subjects the piston to a force which rotates the piston about the center line.

10. A syringe according to claim 9, wherein the second surface on the rod is configured for parallel, linear or punctiform coaction with the corresponding second surface on the piston.

11. A syringe according to claim 1, wherein the first surface on the piston defines an angle of between 85° and 20° with the center line.

* * * * *